United States Patent
Hirakawa et al.

(10) Patent No.: US 12,253,897 B2
(45) Date of Patent: Mar. 18, 2025

(54) INFORMATION PROCESSING SYSTEM AND ELECTRONIC DEVICE COMMUNICATING WITH ANOTHER ELECTRONIC DEVICE

(71) Applicant: SEIKO EPSON CORPORATION, Tokyo (JP)

(72) Inventors: Ryota Hirakawa, Shiojiri (JP); Yasuhiro Terashima, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 70 days.

(21) Appl. No.: 18/190,432

(22) Filed: Mar. 27, 2023

(65) Prior Publication Data

US 2023/0305614 A1    Sep. 28, 2023

(30) Foreign Application Priority Data

Mar. 28, 2022   (JP) ................................ 2022-051339

(51) Int. Cl.
| | |
|---|---|
| *G06F 1/3209* | (2019.01) |
| *A61B 5/00* | (2006.01) |
| *A61B 5/024* | (2006.01) |
| *G06F 1/3234* | (2019.01) |

(52) U.S. Cl.
CPC .......... *G06F 1/3209* (2013.01); *A61B 5/0015* (2013.01); *G06F 1/3278* (2013.01); *A61B 5/024* (2013.01); *A61B 5/681* (2013.01); *A61B 2503/10* (2013.01)

(58) Field of Classification Search
CPC ... G06F 1/3209; G06F 1/3278; A61B 5/0015; A61B 5/024; A61B 5/681; A61B 2503/10
See application file for complete search history.

(56) References Cited

U.S. PATENT DOCUMENTS

| | | | |
|---|---|---|---|
| 11,550,360 B1* | 1/2023 | Passe | G08B 21/0453 |
| 2011/0309930 A1* | 12/2011 | Cecchet | H04W 4/02 |
| | | | 340/539.13 |
| 2012/0302166 A1* | 11/2012 | Yamaoka | H04W 4/80 |
| | | | 455/41.1 |
| 2018/0228448 A1* | 8/2018 | Miyazawa | H04M 11/00 |
| 2019/0166222 A1* | 5/2019 | Hashimoto | H04W 4/20 |
| 2021/0203724 A1* | 7/2021 | Hashimoto | H04L 67/12 |
| 2021/0225505 A1* | 7/2021 | Khare | G06F 11/3089 |
| 2024/0108290 A1* | 4/2024 | Jeon | A61B 5/02055 |

FOREIGN PATENT DOCUMENTS

| | | | |
|---|---|---|---|
| EP | 3091722 A1 * | 11/2016 | ........ H04M 1/72412 |
| JP | 2018-206112 A | 12/2018 | |

* cited by examiner

*Primary Examiner* — Glenn A. Auve
(74) *Attorney, Agent, or Firm* — Oliff PLC

(57) ABSTRACT

An information processing system includes a server and an electronic device. The electronic device communicates with another electronic device, determines whether to operate as a representative device, based on information from the another electronic device, and when the electronic device determines to operate as the representative device, transmits, to the server, detection information detected by the another electronic device.

8 Claims, 7 Drawing Sheets

INFORMATION PROCESSING SYSTEM AND ELECTRONIC DEVICE COMMUNICATING WITH ANOTHER ELECTRONIC DEVICE

The present application is based on, and claims priority from JP Application Serial Number 2022-051339, filed Mar. 28, 2022, the disclosure of which is hereby incorporated by reference herein in its entirety.

BACKGROUND

1. Technical Field

The present disclosure relates to an information processing system and an electronic device.

2. Related Art

Hitherto, there has been known a small-sized device provided with a communication function. The device of this type is required to suppress power consumption to operate for a long time period. For example, JP-A-2018-206112 discloses a system including a master terminal and a slave terminal, as a terminal device that transmits user state information to a management device. In the system of JP-A-2018-206112, the master terminal transmits slave terminal information to a server as a substitute for the slave terminal. With this, power consumption of the slave terminal is reduced.

As described in JP-A-2018-206112, in a configuration in which a specific device performs communication as a substitute for another device, power consumption of the specific device is increased. Further, the specific device is required to be present at a position that enables communication with the another device. Thus, there is a problem in requiring the specific device capable of withstanding large power consumption and maintaining a position that enables communication with the another device.

SUMMARY

An aspect of the present disclosure relates to an information processing system including a server, and an electronic device configured to communicate with another electronic device, determine whether to operate as a representative device, based on information from the another electronic device, and when the electronic device determines to operate as the representative device, transmit, to the server, detection information detected by the another electronic device.

Another aspect of the present disclosure relates to an electronic device including a first communication unit configured to communicate with another electronic device, a second communication unit configured to communicate with a server, and a control unit configured to determine whether the electronic device is to operate as a representative device, based on information from the another electronic device, and when it is determined that the electronic device is to operate as the representative device, transmit, to the server, detection information detected by the another electronic device.

DESCRIPTION OF EXEMPLARY EMBODIMENTS

1. First Exemplary Embodiment

With reference to the drawings, exemplary embodiments of the present disclosure are described below.

1-1. Configuration of Information Processing System

Figure 1:
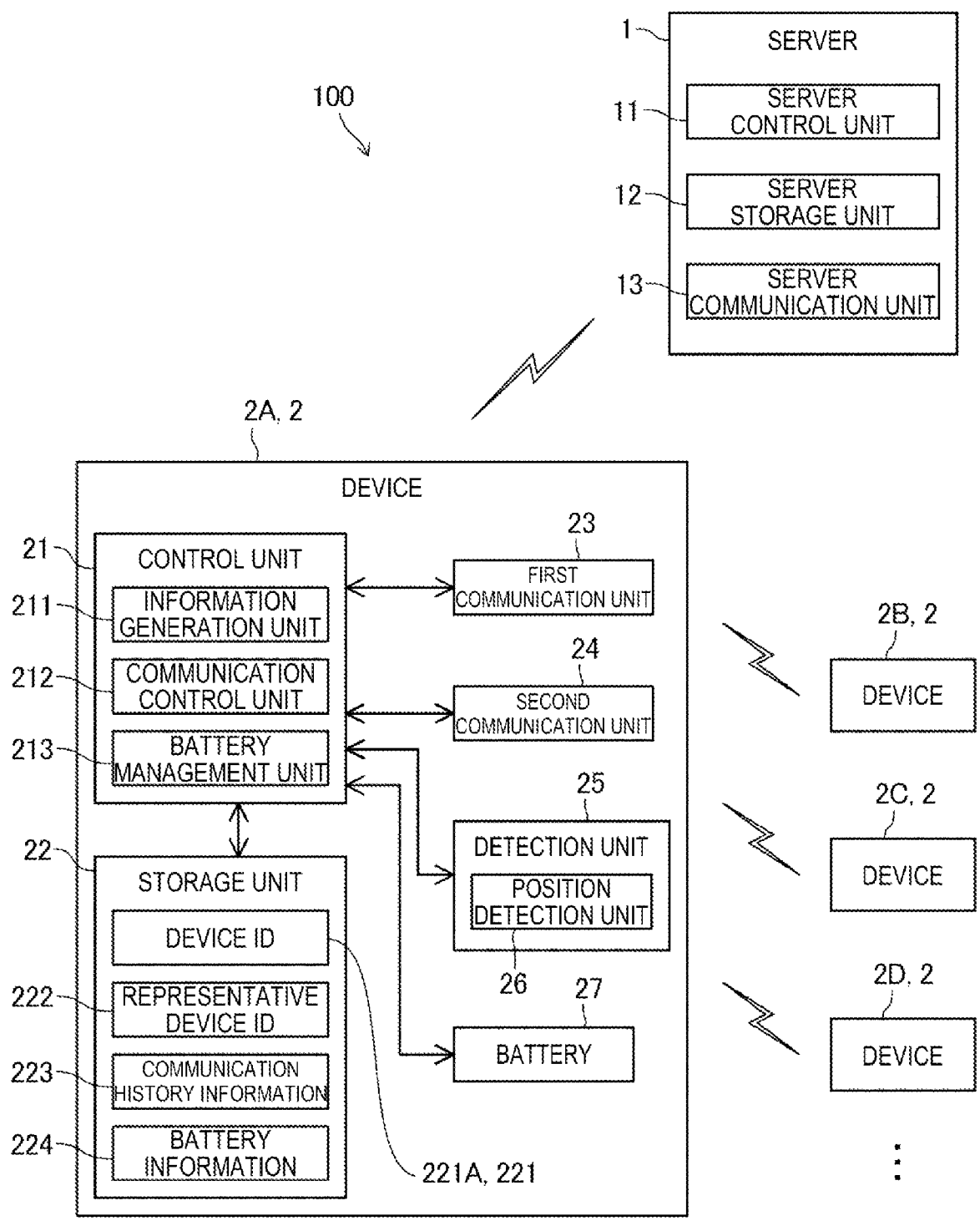
FIG. 1 is a view illustrating a configuration of an information processing system according to a first exemplary embodiment.

FIG. 1 is a diagram illustrating a configuration of an information processing system 100.

The information processing system 100 includes a server 1 and a plurality of devices 2. FIG. 1 illustrates four devices 2A, 2B, 2C, and 2D, which are merely examples, and the number of devices 2 included in the information processing system 100 is not limited. When the devices 2A, 2B, 2C, and 2D and other devices 2 are not distinguished from one another, the devices are collectively referred to as a device 2. The device 2 is an example of an electronic device in the present disclosure.

FIG. 1 illustrates a configuration of the device 2A. The devices 2B, 2C, and 2D and the other devices 2 may be configured similarly to the device 2A. Thus, in the present exemplary embodiment, the configuration of the device 2A is described.

The device 2 included in the information processing system 100 is a portable device. For example, the device 2 is a wearable device on a human body, luggage, or other items, and includes a battery 27 as a battery, as described later. The shape of the device 2 is not limited. For example, examples of the shape of the device 2 include a disc shape and a plate shape, and other shapes may be adopted. For example, the device 2 may be configured as a belt fixed to a human body or luggage. Specifically, the device 2 may be a wristwatch type. Further, the devices 2A, 2B, 2C, and 2D may have shapes different from one another.

The device 2 includes a detection unit 25. The detection unit 25 is a device that performs detection. In the present exemplary embodiment, as an example, description is made on a configuration including a position detection unit 26 that detects a position of the device 2. A target to be detected by the detection unit 25 and detection information are not limited. For example, the detection unit 25 may include a device that detects biological information such as a heart rate, a blood pressure, or a blood oxygenation level of a human body. Further, the detection unit 25 may include a motion sensor that detects acceleration and/or angular velocity, for example, and may be an Inertial Measurement Unit (IMU) obtained by integrating a plurality of sensors. Further, the detection unit 25 may be configured to include an environment sensor for an atmospheric pressure, an altitude, humidity, a temperature, or the like.

The device 2 transmits a detection result detected by the detection unit 25. The information processing system 100 includes the server 1 capable of communicating with the device 2. The server 1 collects and stores the detection result detected by the device 2.

The devices 2A, 2B, 2C, and 2D transmit information containing detection results of the detection units 25. Each of the devices 2A, 2B, 2C, and 2D has a function of executing communication with the server 1 and transmitting the information to the server 1. The device 2 is a portable device, and hence communication between the server 1 and the device 2 may be a relatively long distance communication. Thus, power consumed by the device 2 for executing communication with the server 1 is not smaller than the capacity of the battery 27. Further, the devices 2A, 2B, 2C, and 2D have a function of executing mutual radio communication. Between the device 2 and the device 2 that are at positions close to each other, a near distance radio communication technique can be utilized. Thus, power consumed by the device 2 for executing communication with the device 2 at a close position is smaller than the power consumed by the device 2 for executing communication with the server 1.

In view of this, the information processing system 100 sets any one or more devices 2 included in the information processing system 100, as a representative device. The device 2 that is not set as the representative device is tentatively referred to as a sub device. The sub device transmits the detection result to the device 2 being the representative device via near distance communication. The device 2 being the representative device collectively transmit, to the server 1, the detection result received from the sub device. With this, the number of devices 2 that execute communication with the server 1 can be reduced, and power consumption of the device 2 is suppressed. Thus, a time period during which the device 2 operates with the power of the battery 27 can be increased. The representative device corresponds to an example of a representative device.

Examples of a usage form of the information processing system 100 include a sport event. In a sport event, each contestant wears the device 2 on their body, and the device 2 detects position information. In this case, the server 1 is capable of collecting information relating to a position of each contestant. Further, each of the devices 2 periodically transmit the position information to the server 1, and thus the server 1 is capable of updating a position of each contestant. With this configuration, when power consumption of each of the devices 2 can be suppressed, the device 2 can be utilized during a sport competition that takes place for a long time period.

Hereinafter, a device constituting the information processing system 100 is described in detail.

1-2. Configuration of Device

FIG. 1 illustrates details of the configuration of the device 2A. It can be said that the configuration of the device 2A is a basic configuration of the device 2 in the information processing system 100.

The device 2A includes a control unit 21, a storage unit 22, a first communication unit 23, a second communication unit 24, the detection unit 25, and the battery 27.

Each of the first communication unit 23 and the second communication unit 24 is a radio communication device that executes radio communication under control of the control unit 21.

The second communication unit 24 executes radio communication for a longer distance than the first communication unit 23. In other words, the first communication unit 23 is a device that executes radio communication for a nearer distance than the second communication unit 24, utilizing a near distance radio communication technique.

The first communication unit 23 is a communication device that includes an antenna and a modem, which are not illustrated, and executes data communication between the plurality of devices 2. The first communication unit 23 executes, for example, radio communication conforming to the standard of Bluetooth (trade name) Low Energy. Further, as a communication method executed by the first communication unit 23, UWB (Ultra-wideband), Zigbee (trade name), or other Personal Area Network (PAN) techniques may be adopted. In the following description, description is made on an example in which the device 2 executes communication with the first communication unit 23, using a Bluetooth Mesh technique.

The second communication unit 24 is a communication device that includes an antenna and a modem, which are not illustrated, and transmits and receives various data with the server 1. For example, the second communication unit 24 executes Low Power Wide Area (LPWA) communication. An actual specification for LPWA communication is not limited. For example, the second communication unit 24 executes radio communication conforming to various standards such as NB-IoT, LTE-M, LTE Cat.NB1, Sigfox (trade name), LoRaWAN (trade name), Wi-Fi (trade name) HaLow, Wi-SUN (trade name), ELTRES (trade name), and ZETA (trade name). Further, the second communication unit 24 may have a configuration of executing Long Term Evolution (LTE) communication or 5G cellular communication in place of LPWA communication.

The detection unit 25 a device that executes detection and outputs a detection result, and includes a sensor. The detection unit 25 of the present exemplary embodiment includes the position detection unit 26. The position detection unit 26 is a device that measures a current position of the device 2A. Specifically, the position detection unit 26 is a device that receives a radio wave emitted from an artificial satellite and utilizes Global Navigation Satellite System (GNSS), and the detection unit 25 outputs position information indicating the measurement result obtained by the position detection unit 26.

As described above, the detection unit 25 may include a biological information sensor that detects biological information such as a heart rate, a blood pressure, or a blood oxygenation level of a human body. Further, the detection unit 25 may include a motion sensor that detects acceleration and/or angular velocity, for example. The motion sensor may be an IMU obtained by integrating a plurality of sensors. Further, the detection unit 25 may include an environment sensor for an atmospheric pressure, an altitude, humidity, a temperature, or the like.

The battery 27 supplies power to each unit of the device 2A via a power line, which is not illustrated. The battery 27 is a replaceable primary battery or a secondary battery. The device 2A may include a charging circuit or a charging terminal, which is not illustrated, for charging the battery 27. Further, the device 2A may include a wireless charging device for charging the battery 27.

The control unit 21 is a computer including a processor including one or more Central Processing Units (CPU), a Micro-Processing Unit (MPU), and the like. The control unit 21 controls each unit of the device 2A by causing the processor to execute a program. The control unit 21 includes a non-volatile Read Only Memory (ROM) that stores a program executed by the processor and a Random Access Memory (RAM) constituting a work area relating to processing of the processor. The control unit 21 may be configured as a semiconductor device including a processor, a RAM, and a ROM in an integrated manner. Further, the processor of the control unit 21 may be configured as programmed hardware.

The control unit 21 includes an information generation unit 211, a communication control unit 212, and a battery management unit 213. For example, those are functional units implemented in cooperation of hardware and software when the processor executes a program. Alternatively, there may be adopted a configuration in which the control unit 21 includes hardware corresponding to those functional units.

The storage unit 22 is a non-volatile storage device including a semiconductor memory element or a magnetic storage device. The storage unit 22 stores a device ID 221, a representative device ID 222, communication history information 223, and battery information 224.

The device ID 221 is identification information provided to the device 2A. In the present exemplary embodiment, each of the devices 2 has the device ID 221 that enables identification from the other devices 2. For example, the storage unit 22 of the device 2A stores a device ID 221A that is different from any IDs of the devices 2B, 2C, and 2D. With this, the server 1 is capable of identifying each of the devices 2 included in the information processing system 100, based on the device ID 221.

The representative device ID 222 is the device ID 221 of the device 2 functioning as the representative device. When the device 2A functions as the representative device, in the device 2A, the representative device ID 222 stored in the device 2A is identical to the device ID 221A. Further, for example, when the device 2B functions as the representative device, the representative device ID 222 stored in the device 2A is the device ID 221 of the device 2B.

The representative device ID 222 is a destination to which the device 2A transmits the information to the representative device. Therefore, the representative device ID 222 stored in the device 2A is the device ID 221 of the representative device positioned within a range in which the device 2A is capable of executing communication.

The communication history information 223 is information indicating a history in which the device 2A causes the second communication unit 24 to execute communication. For example, the communication history information 223 contains at least one of the number of times for which the second communication unit 24 executes communication or an accumulated value of a time period during which the second communication unit 24 executes communication, or both of them. The time period during which the second communication unit 24 executes communication may correspond to an operation time period of the second communication unit 24. For example, the communication history information 223 is reset every time when the power of the device 2A is turned on and off, at a timing when the battery 27 is replaced or charged, or at timing of other initialization processes.

The battery information 224 is information indicating a remaining amount in the battery 27. The battery information 224 is updated as the power of the battery 27 is consumed.

The information generation unit 211 generates information, based on an operation of the device 2A. For example, the information generation unit 211 generates detection information relating to the device 2A, based on the detection result output from the detection unit 25. A specific content of the detection information generated by the information generation unit 211 corresponds to a type of information output from the sensor included in the detection unit 25. In the present exemplary embodiment, the detection unit 25 performs measurement, and hence the detection information generated by the information generation unit 211 is position information.

Further, the information generation unit 211 generates the communication history information 223 to store the information in the storage unit 22 or updates the communication history information 223 stored in the storage unit 22 every time when the second communication unit 24 executes communication.

Moreover, the information generation unit 211 generates detection information S1 containing detection information and condition information. The detection information S1 is described later. The condition information is information indicating a load condition of the device 2A. For example, the condition information is information indicating a remaining amount in the battery 27, and is the battery information 224. Further, for example, the condition information is information relating to a history of an operation of the second communication unit 24, and is a part or an entirety of the communication history information 223. The condition information may be information containing all the above-mentioned matters.

When the device 2A operates as the representative device, the communication control unit 212 controls the second communication unit 24 so as to cause the second communication unit 24 to execute communication with the server 1. For example, the communication control unit 212 transmits an information package S2, which is described later, to the server 1.

The communication control unit 212 controls the first communication unit 23 so as to execute communication with the devices 2 other than the device 2A. For example, the communication control unit 212 transmits the detection information S1 to the device 2.

The battery management unit 213 detects a remaining amount in the battery 27, and generates the battery information 224 indicating the remaining amount in the battery 27. The battery management unit 213 execute processing of storing the battery information 224 in the storage unit 22 or processing of updating the battery information 224 stored in the storage unit 22.

1-3. Configuration of Server

The server 1 includes a server control unit 11, a server storage unit 12, and a server communication unit 13.

The server control unit 11 is a computer including a processor including one or more CPUs, a MPU, and the like. The server control unit 11 controls each unit of the server 1 by causing the processor to execute a program in cooperation of software and hardware.

The server control unit 11 may include a non-volatile ROM that stores a program executed by the processor and a RAM constituting a work area relating to processing of the processor. The server control unit 11 may be configured as a semiconductor device including a processor, a RAM, and a ROM in an integrated manner. Further, the processor of the server control unit 11 may be configured as programmed hardware.

The server storage unit 12 is a non-volatile storage device including a semiconductor memory element or a magnetic storage device. The server storage unit 12 stores the information received from the device 2. The server communication unit 13 is a communication device that executes data communication with the device 2. For example, similarly to the second communication unit 24, the server communication unit 13 is a radio communication device that executes radio communication conforming to standards such as LPWA communication. The server communication unit 13 executes communication with the device 2, under control of the server control unit 11.

In the information processing system 100, the server 1 and the device 2 may directly execute communication via LPWA communication or the like. Further, there may be adopted a configuration in which the server 1 and the device 2 are connected to a communication network including various devices such as an access point, a base station, a router, and a gateway, which are not illustrated, and execute mutual data communication via the communication network. In this case, the device 2 is also connected to the server 1 when the second communication unit 24 executes long distance radio communication.

1-4. Operation of Information Processing System

Figure 2:
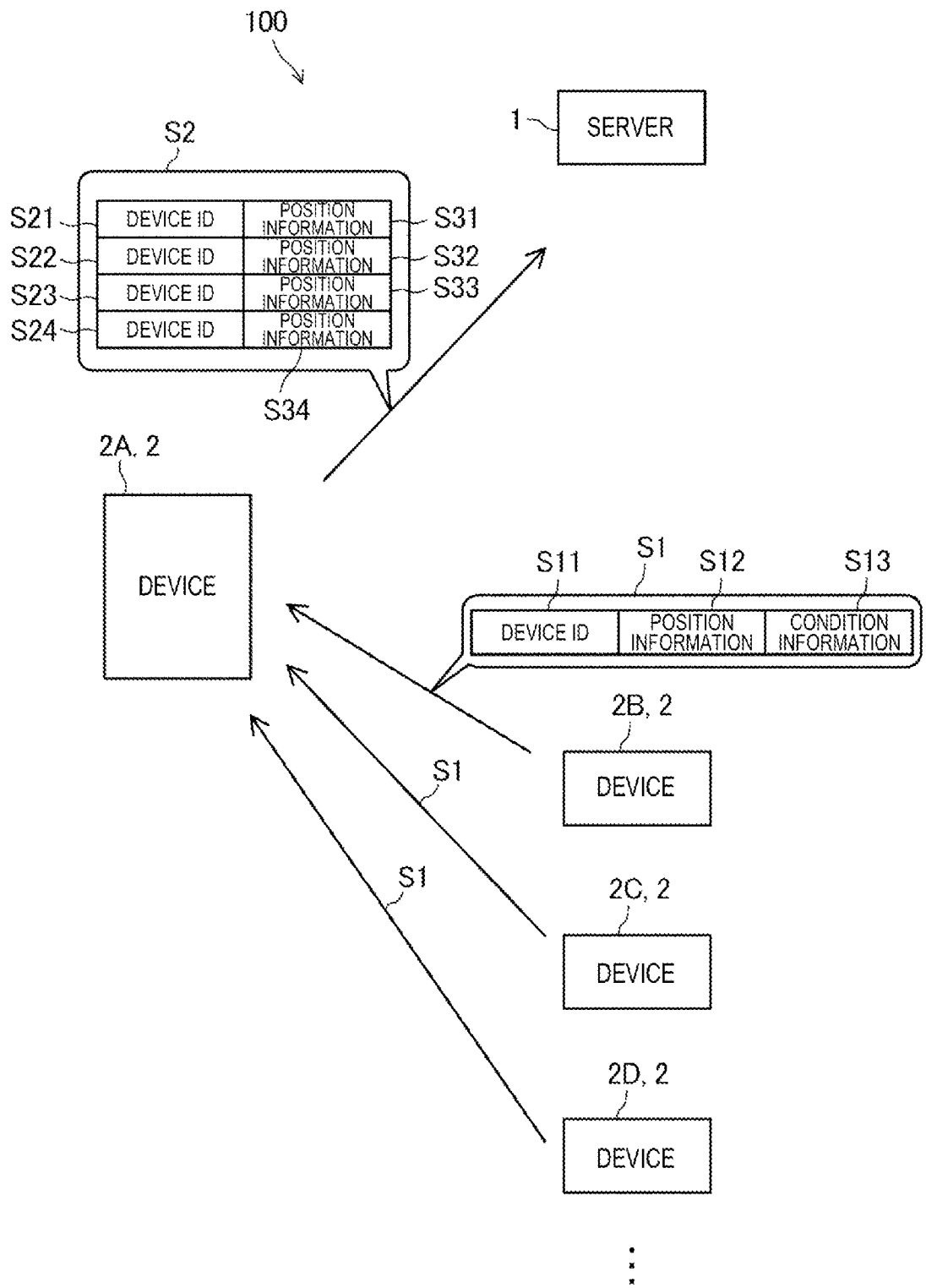
FIG. 2 is a schematic view illustrating an outline of an operation of the information processing system according to the first exemplary embodiment.
Figure 3:
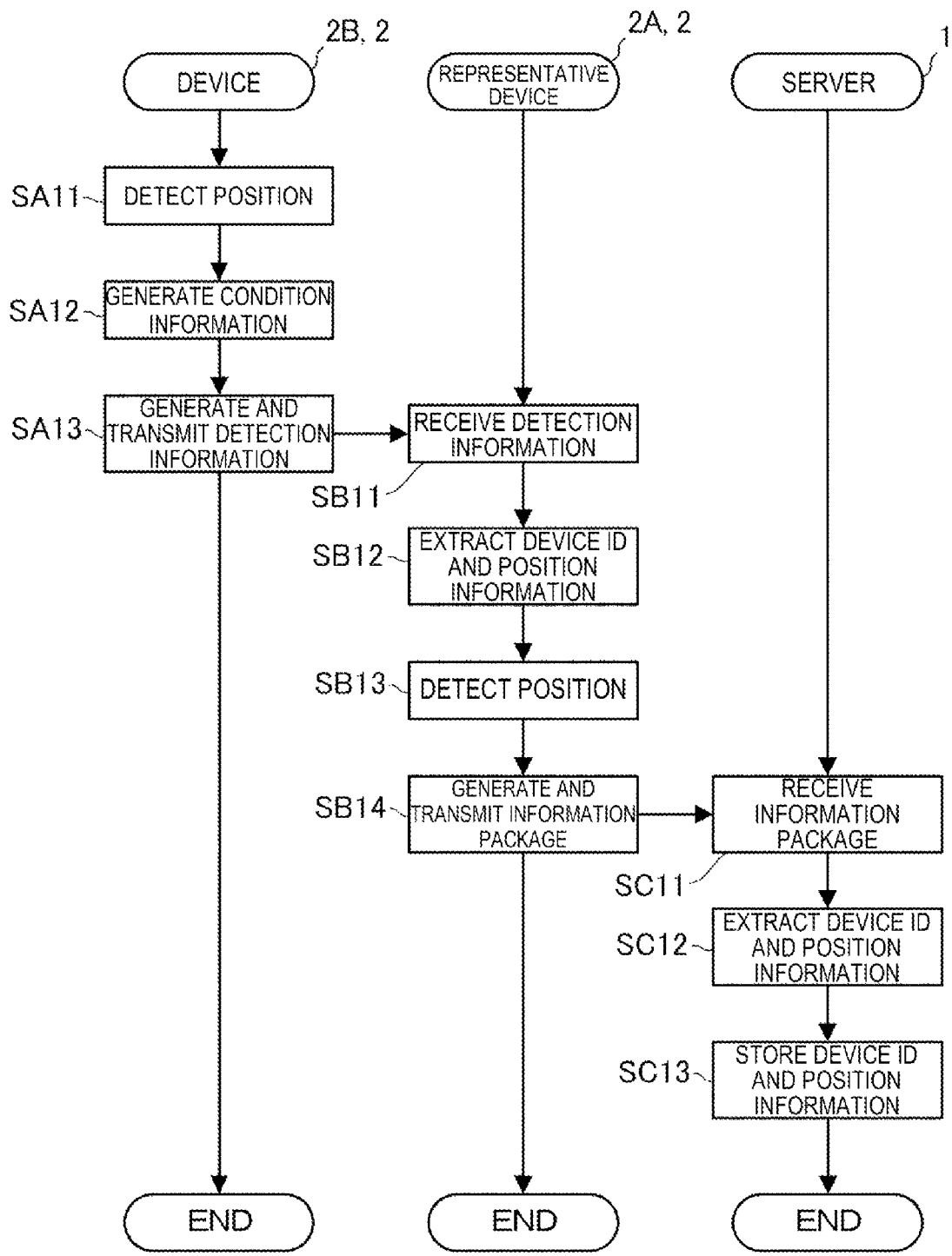
FIG. 3 is a sequence diagram illustrating the operation of the information processing system according to the first exemplary embodiment.

FIG. 2 is a schematic view illustrating an outline of an operation of the information processing system 100 according to the first exemplary embodiment. FIG. 3 is a sequence diagram illustrating the operation of the information processing system 100 according to the first exemplary embodiment. With reference to those drawings, the operation of the information processing system 100 is described.

FIG. 2 and FIG. 3 illustrate an example in which the device 2A operates as the representative device and the devices 2B, 2C, and 2D are connected as the sub devices to the device 2A. In the example of FIG. 2, the device 2A may be referred to as a master device or a substitute device whereas the devices 2B, 2C, and 2D may be referred to as slave devices.

The sequence diagram of FIG. 3 illustrates an operation of the device 2B being an example of the sub device, and an operation of the device 2A being the representative device, and an operation of the server 1.

The device 2B causes the detection unit 25 to execute position detection and the information generation unit 211 to generate position information (Step SA11).

Subsequently, the device 2B generates the condition information (Step SA12).

As described above, the condition information is the communication history information 223 generated by the information generation unit 211 or the battery information 224 generated by the battery management unit 213. When the information generation unit 211 generates the detection information S1, and the communication control unit 212 controls the first communication unit 23, the device 2B transmits the detection information S1 to the device 2A (Step SA13).

As illustrated in FIG. 2, the detection information S1 contains a device ID S11, position information S12, and condition information S13 in association with one another. The device ID S11 is the device ID 221 stored in the device 2B. The position information S12 indicates a position of the device 2B that is detected by the detection unit 25 included in the device 2B. The condition information S13 is information indicating a load condition of the device 2B. For example, the condition information S13 is information indicating a remaining amount in the battery 27 of the device 2B or a history of an operation of the second communication unit 24 of the device 2B. A destination to which the device 2B is transmitted the detection information S1 is designated by the representative device ID 222 stored in the storage unit 22 of the device 2B. In other words, in the example of FIG. 2, the device 2B stores the device ID 221 of the device 2A as the representative device ID 222.

When the device 2A operates as the representative device, the condition information relating to the device 2A corresponds to an example of first condition information, and the condition information S13 relating to the device 2B that is contained in the detection information S1 received by the device 2A corresponds to an example of second condition information.

Similarly, the device 2C and the device 2D execute the operation in Step SA11 to Step SA13 of FIG. 3, and generate and transmit the detection information S1 to the device 2A. The detection information S1 generated by the device 2C contains the device ID S11, the position information S12, and the condition information S13 that relate to the device 2C. The detection information S1 generated by the device 2D contains the device ID S11, the position information S12, and the condition information S13 that relate to the device 2D.

As illustrated in FIG. 3, the device 2A being the representative device causes the first communication unit 23 to receive the detection information S1 transmitted from the device 2B being the sub device (Step SB11), and causes the information generation unit 211 to extract the device ID S11 and the position information S12 from the received detection information S1 (Step SB12).

The device 2A causes the detection unit 25 to execute position detection and the information generation unit 211 to generate position information (Step SB13).

When the information generation unit 211 generates the information package S2, and the communication control unit 212 controls the second communication unit 24, the device 2A transmits the information package S2 to the server 1 (Step SB14). Specifically, the device 2A generates the information package S2 by integrating the device ID S11 and the position information S12 that are extracted in Step SB12, and the device ID 221 of the device 2A and the position information generated in Step SB13.

As illustrated in FIG. 2, the information package S2 is collective data obtained by integrating the information relating to the device 2 being the sub device connected to the device 2A and the information relating to the device 2A. The device 2A transmits the information package S2 to the server 1. Here, the information package S2 is only required to be collective data. For example, as a matter of course, when the device 2A transmits the information package S2 to the server 1, the information package S2 may be divided and transmitted.

The information package S2 illustrated in FIG. 2 contains the device IDs S21, S22, S23, S24, and S25. The device ID S21 is the device ID 221 stored in the device 2A, and the device ID S22 is the device ID 221 stored in the device 2B. The device ID S23 is the device ID 221 stored in the device 2C, and the device ID S24 is the device ID 221 stored in the device 2D.

The information package S2 contains position information S31 associated with the device ID S21. The position information S31 indicates a position detected by the position detection unit 26 of the device 2A. Further, the information package S2 contains position information S32 associated with the device ID S22, position information S33 associated with the device ID S23, and position information S34 associated with the device ID S24. The position information S32 indicates a position detected by the position detection unit 26 of the device 2B, and the position information S33 indicates a position detected by the position detection unit 26 of the device 2C. The position information S31 indicates a position detected by the position detection unit 26 of the device 2D.

In this manner, the information package S2 contains a combination of the position information and the device IDs 221 relating to the devices 2 that recognize the device 2A as the representative device and the device 2A.

Referring back to FIG. 3, the server 1 causes the server communication unit 13 to receive the information package S2 (Step SC11), and extracts the device IDs S21 to S24 and the position information S31 to S34 from the received information package S2 (Step SC12). The server 1 stores the information extracted from the information package S2, in the server storage unit 12. The server storage unit 12 stores the device ID S21 and the position information S31 in association with each other. Similarly, the server storage unit 12 stores the position information S32 in association with the device ID S22, the position information S33 in association with the device ID S23, and the position information S34 in association with the device ID S24.

In this manner, the device 2A transmits the information package S2 to the server 1, and thus the server 1 is capable of acquiring the position information relating to each of the devices 2A, 2B, 2C, and 2D. With this configuration, the device 2 that executes communication with the server 1 via LPWA communication is limited to the device 2A, and the devices 2B, 2C, and 2D are not required to execute LPWA communication. Thus, power consumption of the devices 2B, 2C, and 2D can be suppressed, and the position information relating to the devices 2B, 2C, and 2D can be transmitted to the server 1.

In the example of FIG. 2, there is illustrated the configuration in which the information package S2 contains all the device IDs S21 to S22 and the position information S31 to S34 relating to the devices 2A, 2B, 2C, and 2D, but the number of information pieces contained in the information package S2 is not limited. Further, the number of pieces of the detection information S1 received by the device 2A is not limited.

The device 2A may execute reception in Step SB11 every time when any one of the devices 2B, 2C, or 2D transmits the detection information S1, or may repeatedly execute Step SB11, Step SB12, and Step SB13 periodically as set in advance. For example, the device 2A may execute Step SB11 every period T1, and may execute Step SB12 to Step SB14 every period T2. In this case, the period T2 is longer than the period T1. Further, the information package S2 generated by the device 2A is only required to contain the device ID and the position information relating to at least part of the devices 2A, 2B, 2C, and 2D. The period T2 corresponds to an example of a second period in the present disclosure.

Further, the devices 2B, 2C, and 2D execute Step SA11 to Step SA13 of FIG. 3 every predetermined period T3 that is set in advance. The period T3 is shorter than the period T2. Further, the period T3 may be equal to the period T1, or may be a period longer or shorter than the period T1.

In the information processing system 100, the device 2 operating as the representative device is not fixed, and can be changed. For example, a state in which the device 2A operates as the representative device can be shifted to a state in which any one of the devices 2B, 2C, or 2D operates as the representative device.

As a method of changing the representative device, the present exemplary embodiment discloses an example in which each of the devices 2 determines whether to operate as the representative device or operate as the sub device. In this operation example, the device 2 utilizes the condition information indicating a load condition of the device 2.

1-5. Operation Relating to Change of Representative Device

Figure 4:
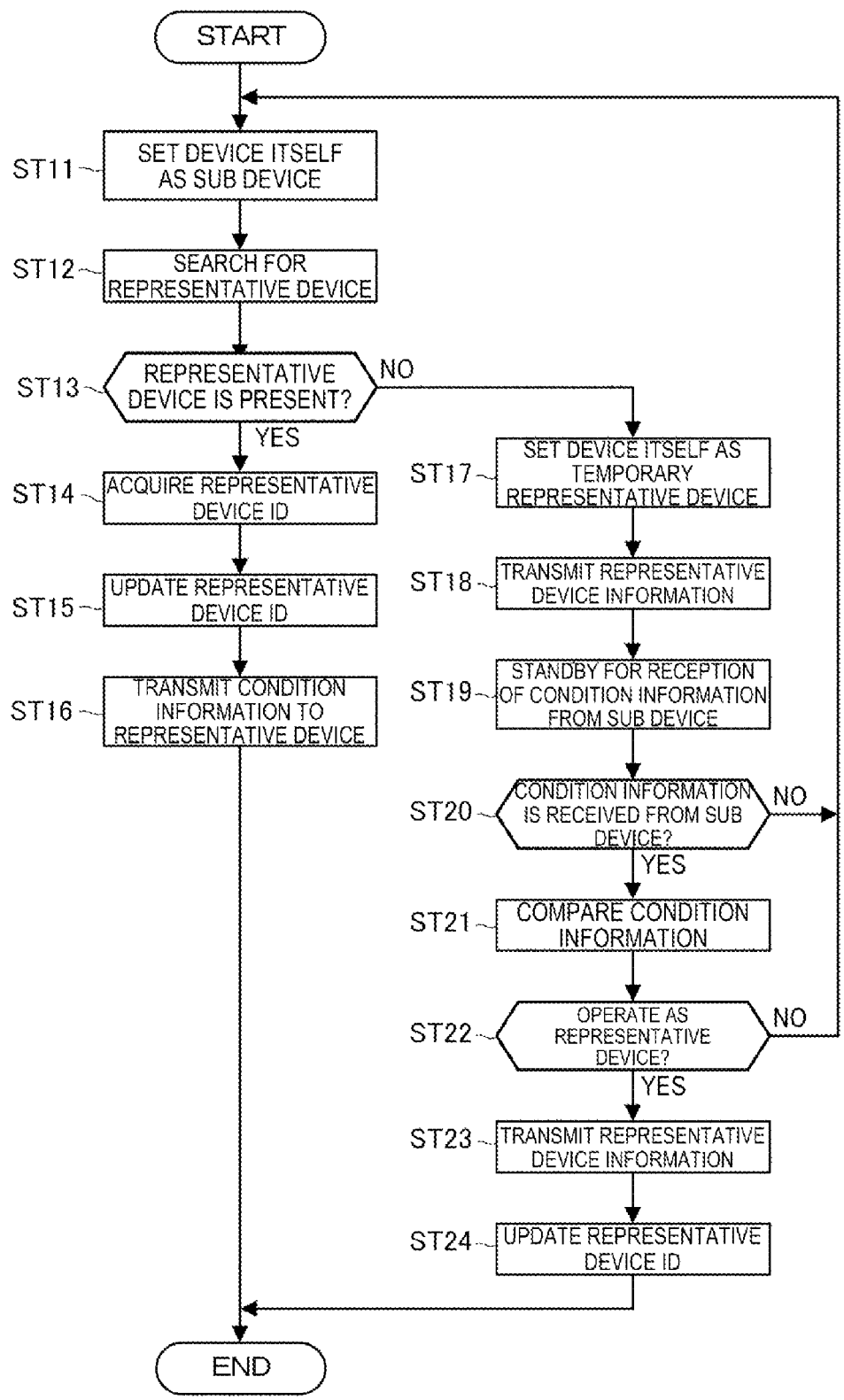
FIG. 4 is a flowchart illustrating an operation of a device according to the first exemplary embodiment.

FIG. 4 is a flowchart illustrating an operation of the device 2 according to the first exemplary embodiment.

The operation illustrated in FIG. 4 is executed by the device 2 operating as the representative device, among the devices 2A, 2B, 2C, and 2D and other devices 2. Here, description is made on an example the device 2A executes the operation of FIG. 4. A period T4 being an execution period of the operation of FIG. 4 is longer than the period T2 described above. The period T4 corresponds to an example of a first period in the present disclosure.

Step ST11 to Step ST24 are executed by the control unit 21.

The device 2A sets the device itself, that is, the device 2A as the sub device (Step ST11). The device 2A searches for the representative device positioned within a range in which the first communication unit 23 is capable of executing communication (Step ST12). For example, the device 2A causes the first communication unit 23 to execute Bluetooth Mesh network communication, and searches for the representative device present in Bluetooth Mesh.

Through searching in Step ST12, the device 2A determines whether the representative device is found, in other words, whether the representative device other than the device 2A is present (Step ST13). For example, when the device 2A receives the representative device information, which is described later, for example, the device 2A determines that the representative device is present.

When the device 2A determines that the representative device is present (YES in Step ST13), the device 2A acquires the device ID of the representative device being found, as the representative device ID (Step ST14). In other words, the device 2A executes the same operation as that when the device 2A determines not to operate as the representative device. The device 2A updates the representative device ID 222 stored in the device 2A, based on the device ID acquired in Step ST14 (Step ST15). Moreover, the device 2A generates and transmits the condition information to the representative device (Step ST16). In Step ST16, the device 2A may generate and transmit the detection information S1 described above. Further, the operation in Step ST16 may be a common operation to the operation of the device 2B that is illustrated in FIG. 3.

Meanwhile, when the device 2A determines that the representative device is not present (NO in Step ST13), the device 2A sets the device 2A as a temporary representative device (Step ST17).

The device 2A causes the first communication unit 23 to transmit the representative device information (Step ST18). The representative device information is information indication that the device 2A is the representative device, and the representative device information is transmitted to all the devices 2 to which the first communication units 23 belong, in the Bluetooth Mesh network. With this, the devices 2 other than the device 2A are notified that the device 2A is the representative device. The representative device information corresponds to an example of representative device information in the present disclosure.

The device 2A stands by for reception of the condition information from the device 2 being the sub device (Step ST19). Here, for example, the device 2A stands by for the condition information transmitted from the devices 2 other than the device 2A in Step ST16 or a similar operation to that of the device 2B of FIG. 3.

In Step ST19, the device 2A attempts to receive the detection information S1 containing the condition information or the condition information during a standby period that is set in advance. The device 2A determines whether the condition information is received during the standby period (Step ST20). In Step ST20, when, during the standby period, the device 2A receives the condition information from the number of devices 2 or more, the number being a threshold value N that is set in advance, the device 2A performs affirmative determination (YES in Step ST20). The threshold value may be one, or a number equal to or greater than two. Further, when, during the standby period, the device 2A receives the condition information only from the number of devices 2, the number being less than the threshold value N, the device 2A performs negative determination (NO in Step ST20).

When negative determination is performed in Step ST20 (NO in Step ST20), the device 2A returns to Step ST11.

When affirmative determination is performed in Step ST20 (YES in Step ST20), the device 2A compares the condition information received in Step ST19 (Step ST21). The device 2A determines whether the device 2A is to operate as the representative device, based on the comparison result in Step ST21 (Step ST22).

Step ST21 and Step ST22 are described in detail.

The device 2A compares the condition information received from the other devices 2 and the condition information relating to the device 2A, and thus selects the device 2 under a light load condition as the representative device. For example, the condition information is the communication history information 223. Specifically, the condition information is the number of times of communication executed by the second communication unit 24 and the time period of communication executed by the second communication unit 24 that are indicated in the communication history information 223. Further, the condition information indicates a remaining amount of the power of the battery 27 indicated in the battery information 224.

For example, when a remaining amount in the battery 27 is used as the condition information, the device 2A selects the device 2 with the largest remaining amount in the battery 27 as the representative device in Step ST21 and Step ST22. When the device 2 with the largest remaining amount in the battery 27 is the device 2A, the device 2A determines that the device 2A is to operate as the representative device (YES in Step ST22). Further, when the device 2 with the largest remaining amount in the battery 27 is not the device 2A, the device 2A determines that the device 2A is not to operate as the representative device (NO in Step ST22). In this example, the device 2 with a little remaining amount in the battery 27 can be prevented from causing the second communication unit 24 to execute communication. Therefore, imbalance of remaining amounts in the batteries 27 of the devices 2 constituting the Bluetooth Mesh network can be prevented, and a state in which a large number of devices 2 are driven for a long time period can be achieved.

Further, for example, when the number of times of communication executed by the second communication unit 24 is used as the condition information, the device 2A selects the device 2 with the least number of times of communication executed by the second communication unit 24 as the representative device in Step ST21 and Step ST22. When the device 2 with the least number of times of communication executed by the second communication unit 24 is the device 2A, the device 2A determines that the device 2A is to operate as the representative device (YES in Step ST22). Further, when the device 2 with the least number of times of communication executed by the second communication unit 24 is not the device 2A, the device 2A determines that the device 2A is not to operate as the representative device (NO in Step ST22). Power consumed by communication executed by the second communication unit 24 accounts for a large percentage of the power consumption of the device 2. Thus, the number of times of communication executed by the second communication unit 24 can be utilized as a guide for power consumed by the device 2. Therefore, in this example, the device 2 with a large power consumption amount can be prevented from causing the second communication unit 24 to execute communication. Therefore, imbalance of remaining amounts in the batteries 27 of the devices 2 constituting the Bluetooth Mesh network can be prevented, and a state in which a large number of devices 2 are driven for a long time period can be achieved.

Further, for example, when the time period of communication executed by the second communication unit 24 is used as the condition information, the device 2A selects the device 2 with the least accumulated value of the time period of communication executed by the second communication unit 24 as the representative device in Step ST21 and Step ST22. When the device 2 with the least accumulated value of the time period of communication executed by the second communication unit 24 is the device 2A, the device 2A determines that the device 2A is to operate as the representative device (YES in Step ST22). Further, when the device 2 with the least accumulated value of the time period of communication executed by the second communication unit 24 is not the device 2A, the device 2A determines that the device 2A is not to operate as the representative device (NO in Step ST22). Power consumed by communication executed by the second communication unit 24 accounts for a large percentage of the power consumption of the device 2. Thus, the accumulated value of the time period of communication executed by the second communication unit 24 can be utilized as a guide for power consumed by the device 2. Therefore, in this example, the device 2 with a large power consumption amount can be prevented from causing the second communication unit 24 to execute communication. Therefore, imbalance of remaining amounts in the batteries 27 of the devices 2 constituting the Bluetooth Mesh network can be prevented, and a state in which a large number of devices 2 are driven for a long time period can be achieved.

When the device 2A determines not to operate as the representative device (NO in Step ST22), the device 2A returns to Step ST11. When the device 2A determines to operate as the representative device (YES in Step ST22), the device 2A transmits the representative device information to the first communication unit 23 similarly in Step ST18 (Step ST23). The device 2A causes the device ID 221 of the device 2A to update the representative device ID 222 stored in the device 2A (Step ST24), and terminates the present processing.

In the information processing system 100, each of the devices 2A, 2B, 2C, and 2D and other devices 2 executes the operation of FIG. 4, and determines whether to operate as the representative device. With this, among the plurality of devices 2 mutually constituting the Bluetooth Mesh network, the device 2 under a light load condition operates as the representative device.

Determination in Step ST21 and Step ST22 is merely an example. For example, two or more selected from the remaining amount in the battery 27, the number of times of communication executed by the second communication unit 24, and the accumulated value of the time period of communication executed by the second communication unit 24 may be combined to identify the device 2 under a light load condition. With this, the device 2A may determine whether to operate as the representative device. The same holds true to the devices 2 other than the device 2A.

1-6. Effects and the Like

As described above, the information processing system 100 according to the present disclosure includes the server 1, and the device 2 that communicates with other devices 2, determines whether to operate as the representative device, based on the information from the other devices 2, and when the device 2 determines to operate as the representative device, transmits, to the server 1, the detection information detected by the other devices 2.

With this, any one of the plurality of devices 2 that is capable of communicating with the server 1 functions as the representative device, and the representative device transmits, to the server 1, the detection information transmitted to the other devices 2. Thus, power consumption of the plurality of devices 2 as a whole can be suppressed. Further, the device 2 determines whether to operate as the representative device, and thus the representative device is determined as appropriate from the plurality of devices 2. Thus, a load can be prevented from being imposed on a specific device 2, and a state in which a large number of devices 2 are driven for a long time period can be achieved.

The device 2 included in the information processing system 100 includes the first communication unit 23 that communicates with the other devices 2, the second communication unit 24 that communicates with the server 1, and the control unit 21 that determines whether the device 2 is to operate as the representative device, based on the information from the other devices 2, and when it is determined that the device 2 is to operate as the representative device, transmits, to the server 1, the detection information detected by the other devices 2.

With this, in the information processing system 100 including the plurality of devices 2, any one of the plurality of devices 2 that is capable of communicating with the server 1 functions as the representative device, and the representative device transmits, to the server 1, the detection information transmitted to the other devices 2. Thus, power consumption of the plurality of devices 2 as a whole can be suppressed. Further, the device 2 determines whether to operate as the representative device, and thus the representative device is determined as appropriate from the plurality of devices 2. Thus, a load can be prevented from being imposed on a specific device 2, and a state in which a large number of devices 2 are driven for a long time period can be achieved.

The device 2 of the first exemplary embodiment transmits, to the other devices 2, the representative device information indicating that the device 2 operates as the representative device when the device 2 determines to operate as the representative device, and the other devices 2 determine not to operate as the representative device when the other devices 2 receive the representative device information. For example, as illustrated in FIG. 4, when the device 2A receives the representative device information and thus determines that the representative device other than the device 2A is present, the device 2A operates as the sub device. Thus, the plurality of devices 2 that are positioned within a range in which the first communication units 23 are capable of executing mutual communication can be prevented from operating as the representative device, and power consumption of the plurality of devices 2 as a whole can be suppressed. With this, a load can be prevented from being imposed on a specific device 2, and a state in which a large number of devices 2 are driven for a long time period can be achieved.

The control unit 21 of the device 2 compares the first condition information indicating the load condition of the device 2 and the second condition information indicating the load conditions of the other devices 2 and received from the other devices 2, and determines whether to operate as the representative device.

With this, the device 2 itself determines whether to operate as the representative device, based on the load conditions of the plurality of devices 2. As a result, the representative device is selected based on the load condition of the device 2. Therefore, a load can be prevented more securely from being imposed on a specific device 2.

The device 2 receives the detection information and the device IDs of the other devices 2.

With this, the other devices 2 receives the detection information containing the detection result of the detection unit 25 in association with the device ID 221 of the device 2. Thus, the device 2 is capable of collecting the detection information relating to the other devices 2 in a distinguishable manner with the device IDs 221.

The device 2 receives the position information and the device IDs of the other devices 2.

With this, the device 2 receives the position information relating to the other devices 2 in association with the device IDs 221 of the other devices 2. Thus, the device 2 is capable of collecting the position information relating to the other devices 2 in a distinguishable manner with the device IDs 221.

The device 2 periodically determines whether to operate as the representative device every first period. When the device 2 determines to operate as the representative device, the device 2 periodically executes an operation of transmitting the detection information to the server 1 every second period shorter than the first period.

With this, the period of the processing in which the representative device is potentially changed is longer than the period of the processing in which the representative device transmits the information package S2. Thus, a state in which the operation of transmitting the information package S2 to the server 1 is delayed due to changing of the representative device can be prevented, and the information package S2 can be transmitted to the server 1 more securely.

For example, the period T4 being the period in which the processing of FIG. 4 is executed may be 10 minutes, and the period T2 being the period in which the representative device transmits the information package S2 may be 30 seconds. In this case, the representative device is not changed for 10 minutes after the representative device is determined. Therefore, frequent changing of the representative device can be suppressed, and the operation of transmitting the information package S2 from the representative device to the server 1 can stably be executed.

In the exemplary embodiment described above, description is made on the example in which the device 2 operating as the representative device executes the operation of FIG. 4, but the device 2 operating as the sub device may execute the operation. Specifically, when communication with the representative device cannot be established, the device 2 operating as the sub device executes the operation of FIG. 4. For example, when the representative device cannot be detected in Bluetooth Mesh while the device 2 operates as the sub device, the device 2 executes the operation of FIG. 4. With this, when communication with the representative device cannot be established due to increase of a distance between the representative device and the sub device or other communication failures, the device 2 quickly finds a new representative device, or the device itself operates as the representative device. Thus, the server 1 is capable of collecting the detection information relating to each of the devices 2 of the information processing system 100 in a more reliable manner.

2. Second Exemplary Embodiment

Figure 5:
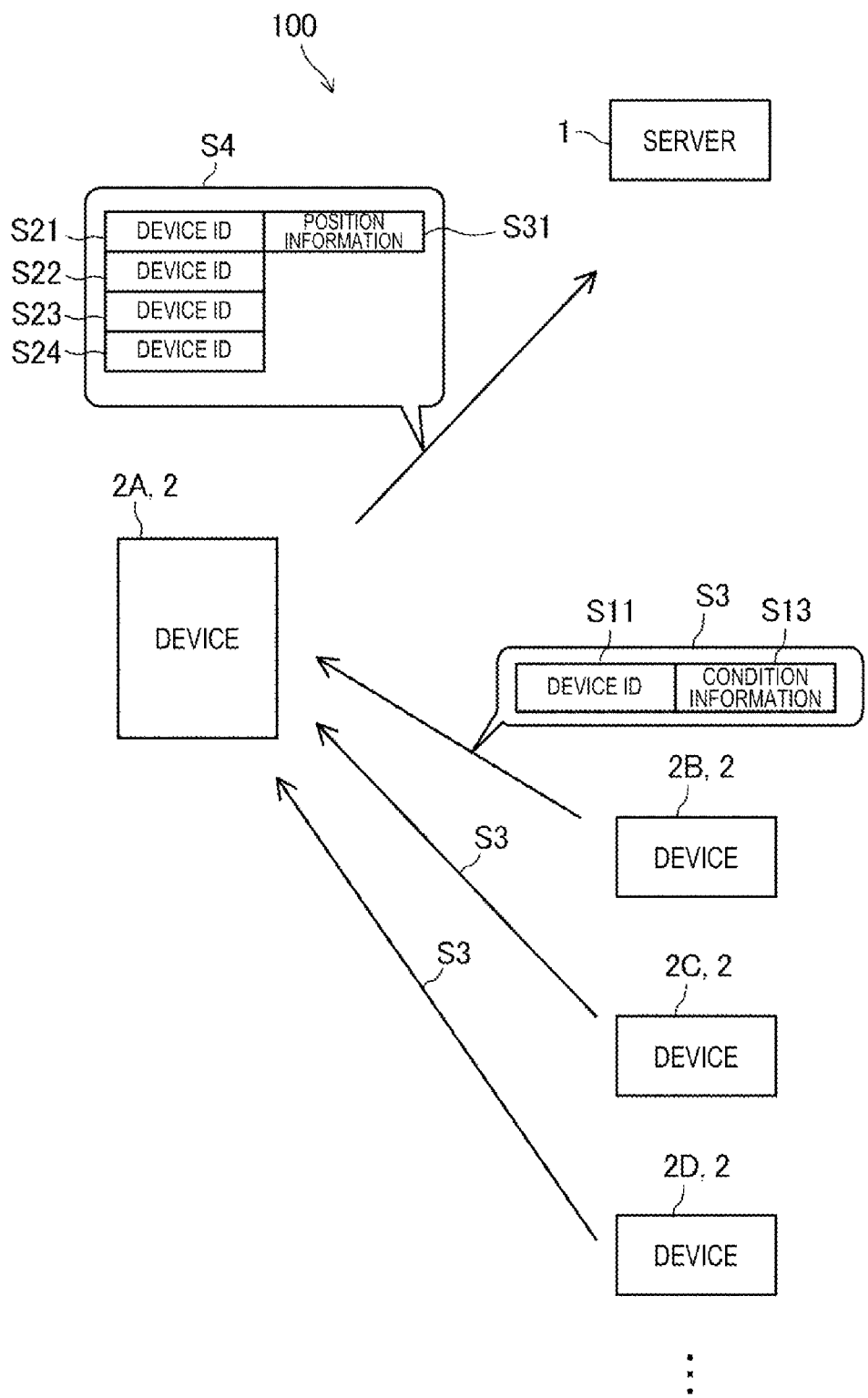
FIG. 5 is a schematic view illustrating an outline of an operation of an information processing system according to a second exemplary embodiment.
Figure 6:
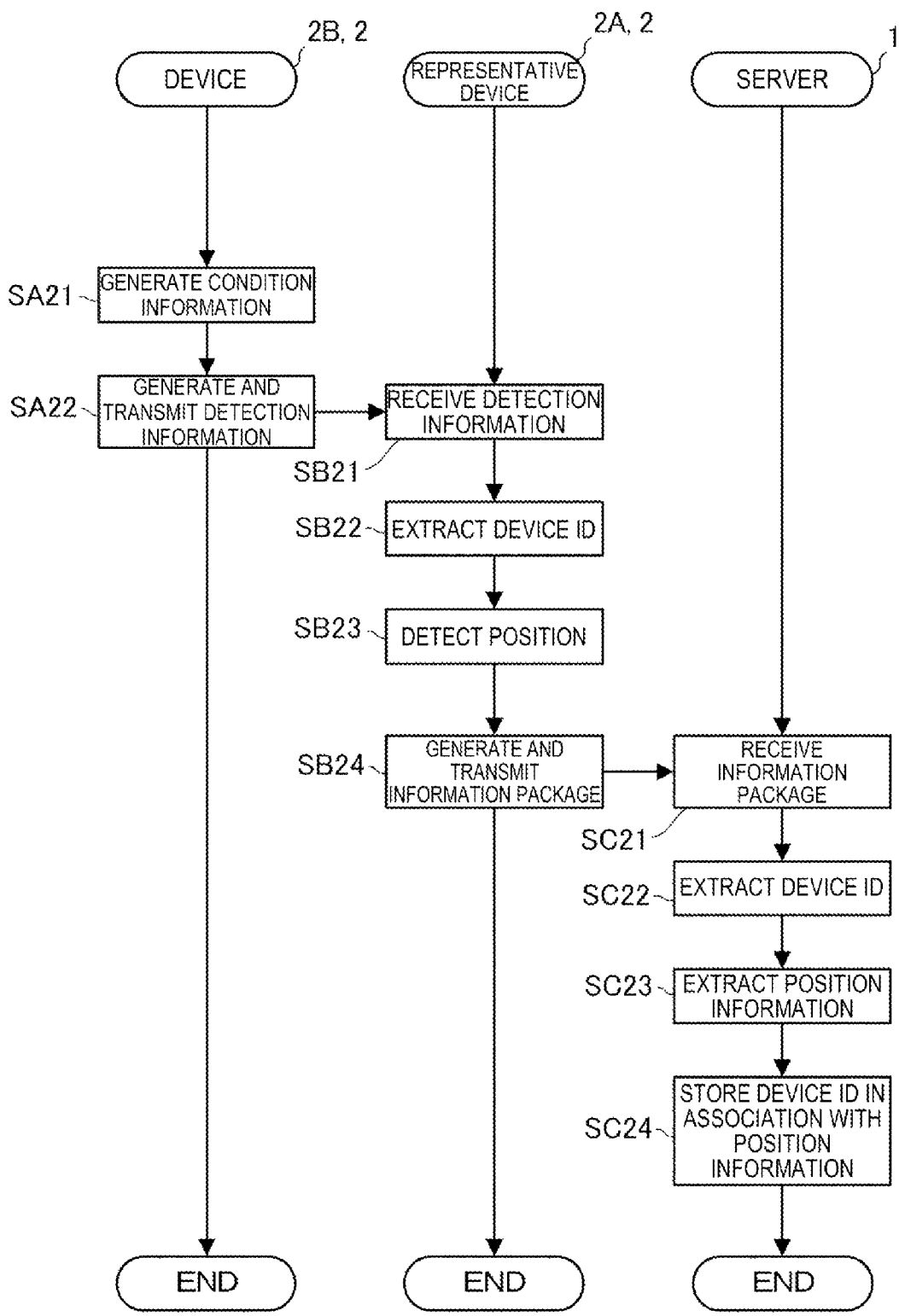
FIG. 6 is a sequence diagram illustrating the operation of the information processing system according to the second exemplary embodiment.

FIG. 5 is a schematic view illustrating an outline of an operation of the information processing system 100 according to a second exemplary embodiment. FIG. 6 is a sequence diagram illustrating the operation of the information processing system 100 according to the second exemplary embodiment. Note that, in FIG. 5, common configurations to those of the information processing system 100 described in the first exemplary embodiment are denoted with identical reference symbols, and description thereof is omitted.

In the second exemplary embodiment, in the information processing system 100, the position information collected by the server 1 is the position information relating to the device operating as the representative device. In other words, the position information relating to the device 2 operating as the representative device is regarded as the position information relating to the device 2 being the sub device in the processing.

In the example of FIG. 5, the devices 2B, 2C, and 2D operate as the sub devices. The devices 2B, 2C, and 2D transmit detection information S3 to the device 2A being the representative device. The detection information S3 does not contain the position information S12, which is different from the detection information S1 of the first exemplary embodiment. In other words, the detection information S3 contains the device ID S11 and the condition information S13.

As illustrated in FIG. 6, the device 2B does not execute an operation corresponding to Step SA11 (FIG. 3), and generates the condition information (Step SA21). An operation of Step SA21 is similar to that of Step SA12. The device 2B causes the information generation unit 211 to generate the detection information S3, and causes the first communication unit 23 to transmit the detection information S3 to the device 2A (Step SA22).

The device 2C and the device 2D similarly execute the operation in Step SA21 and Step SA22 of FIG. 6, generate and transmit the detection information S3 to the device 2A. The detection information S3 generated by the device 2C contains the device ID S11 and the condition information S13 that relate to the device 2C, and the detection information S3 generated by the device 2D contains the device ID S11 and the condition information S13 that relate to the device 2D.

The device 2A receives the detection information S3 from the devices 2B, 2C, and 2D (Step SB21), and extracts the device IDs S11 from the detection information S3 (Step SB22). Moreover, the device 2A causes the detection unit 25 of the device 2A to detect a position of the device 2A (Step SB23).

Here, the device 2A generates the information package S2 containing the position information detected in Step SB23 and the device IDs S11 extracted in Step SB22 (Step SB24). As illustrated in FIG. 5, an information package S4 generated in Step SB24 contains the device IDs S21 to S24 of the device 2A and the devices 2B, 2C, and 2D being the sub devices, and contains the position information S31 relating to the device 2A. In other words, the position information relating to the devices 2B, 2C, and 2D is not contained in the information package S4.

The server 1 receives the information package S4 transmitted from the device 2A (Step SC21), and extracts the device IDs S21 to S24 from the received information package S4 (Step SC22). Moreover, the server 1 extracts the position information S31 from the information package S4 (Step SC23).

The server 1 associates the position information S31 extracted in Step SC23 with the device IDs S21 to S24 extracted in Step SC22, respectively, and stores the information and the IDs in the server storage unit 12 (Step SC24).

With this, the position information S31 is stored in association with the device ID S21 in the server storage unit 12. Further, the position information S31 is associated with the device IDs S22, S23, and S24, respectively, and is stored in the server storage unit 12.

In the second exemplary embodiment, when the device 2 does not operate as the representative device, the device 2 transmits, to the device 2 being the representative device, the detection information S3 that does not contain the position information and contains the device ID S11 and the condition information S13. The device 2A operating as the representative device generates the information package S4, based on the position information relating to the device 2A and the device ID S11 contained in the detection information S3 transmitted from the device 2 operating as the sub device. Specifically, the device 2A generates the information package S4 containing the device ID S21 of the device 2A, the device IDs S22 to S24 of one or the plurality of devices 2 transmitting the detection information S3, and the position information S31 relating to the device 2A. The device 2A transmits the information package S4 to the server 1, and the server 1 associates the position information S31 with the device IDs S21 to S24, respectively, based on the information package S4 and stores the information and the IDs in the server storage unit 12.

The device 2A being the representative device and the device 2 connected as the sub device to the device 2A via the first communication units 23 are positioned within a range in which the first communication units 23 are capable of executing mutual communication. The first communication unit 23 executes near distance communication. Thus, the distance between the device 2A and the device 2 is small, and hence the position of the device 2A can be regarded as the positions of the other devices 2. Thus, the position detection operation executed by the device 2 operating as the sub device can be reduced, and a data amount of the detection information S3 transmitted from the device 2 can be suppressed. With this, a power consumption amount of the device 2 operating as the sub device can further be reduced. Further, a data amount of the information package S4 is smaller than that in the configuration of the first exemplary embodiment, and hence a power consumption amount of the device 2A operating as the representative device can be suppressed.

3. Third Exemplary Embodiment

In a third exemplary embodiment, in the information processing system 100, the device 2 operating as the sub device transmits speed information to the representative device. For example, the information generation unit 211 calculates the speed information, based on a position change detected by the position detection unit 26.

Figure 7:
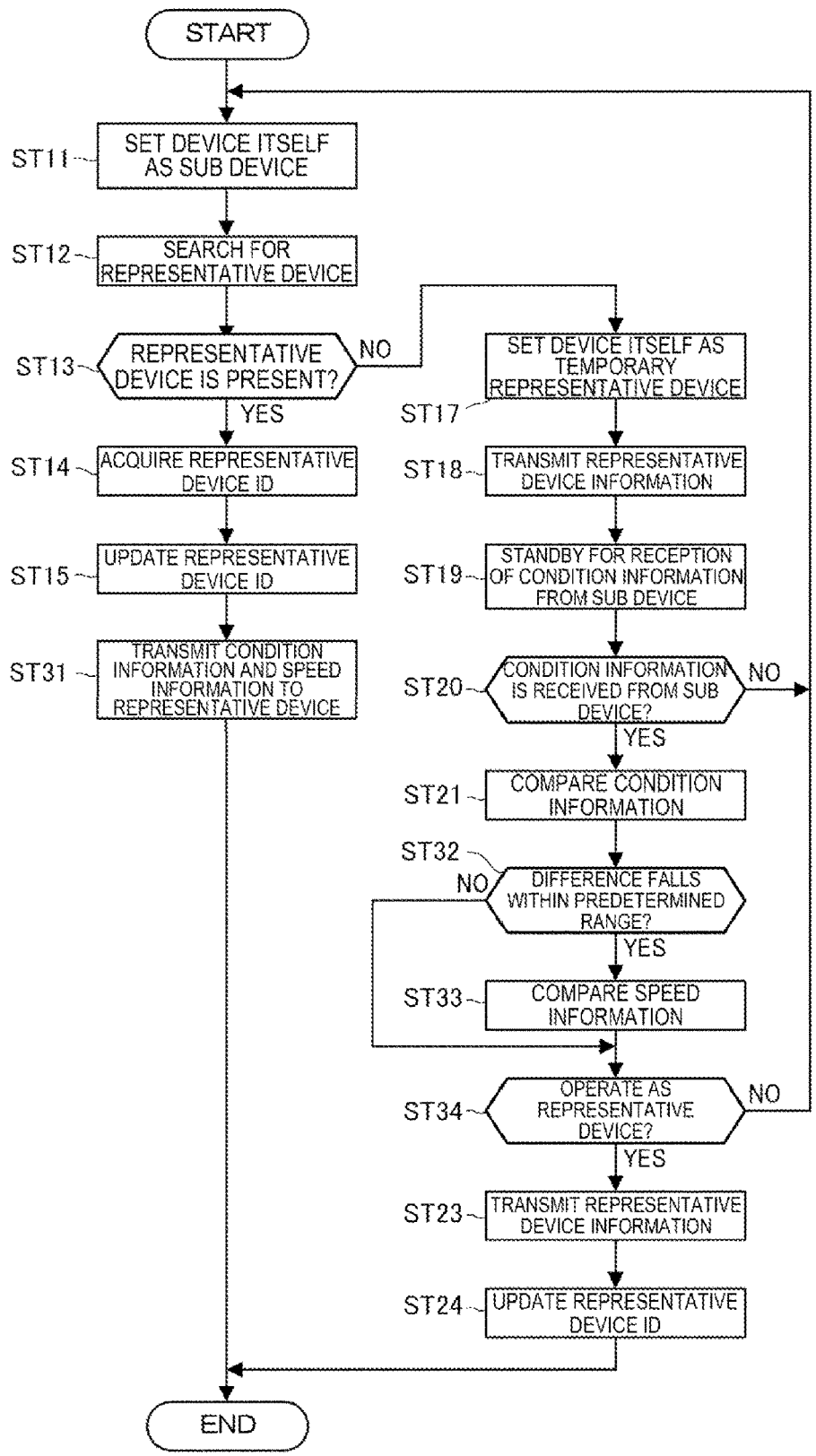
FIG. 7 is a flowchart illustrating an operation of a device according to a third exemplary embodiment.

FIG. 7 is a flowchart illustrating an operation of the device 2 according to the third exemplary embodiment. In place of the operation of FIG. 4, the operation of FIG. 7 is executed by the device 2 operating as the representative device. Here, description is made on an example the device 2A executes the operation of FIG. 7. The operation of FIG. 7 is executed every period T4 similarly to the operation of FIG. 4. In the operation of FIG. 7, common processing to that of FIG. 4 is denoted with an identical step number, and description thereof is omitted.

Step ST11 to Step ST24 and Step ST31 to Step ST34 are executed by the control unit 21.

When, through searching in Step ST12, the representative device is found (YES in Step ST13), the device 2A acquires the representative device ID (Step ST14), and updates the representative device ID 222 (Step ST15). After that, the device 2A generates and transmits the condition information and the speed information to the representative device (Step ST31). In Step ST31, the device 2A may transmit the detection information S1 containing the device ID S11, the position information S12, the condition information S13, and the speed information indicating a speed of the device 2.

Meanwhile, when the device 2A determines that the representative device is not present (NO in Step ST13), the device 2A executes the processing in Step ST17 to Step ST20.

In Step ST21, the device 2A compares the condition information received in Step ST19 (Step ST21). The device 2A determines whether a difference in the condition information falls within a predetermined range, based on the comparison result in Step ST21 Step ST31).

For example, when a remaining amount in the battery 27 is adopted as the condition information, the device 2A compares remaining amounts in the batteries 27 that are received from the other devices 2 and a remaining amount in the battery 27 of the device 2A in Step ST21. Based on the comparison result in Step ST21, the device 2A determines whether a difference between the remaining amounts in the batteries 27 falls within a predetermined range in Step ST31.

Further, for example, when the number of times of communication executed by the second communication unit 24 is adopted as the condition information, the device 2A compares the numbers of times of communication executed by the second communication units 24 that are received from the other devices 2 and the number of times of communication executed by the second communication unit 24 of the device 2A in Step ST21. Based on the comparison result in Step ST21, the device 2A determines whether a difference between the numbers of times of communication executed by the second communication units 24 falls within a predetermined range in Step ST31.

Further, for example, when the time period of communication executed by the second communication unit 24 is adopted as the condition information, the device 2A compares the time periods of communication executed by the second communication units 24 that are received from the other devices 2 and the time period of communication executed by the second communication unit 24 of the device 2A in Step ST21. Based on the comparison result in Step ST21, the device 2A determines whether a difference between the time periods of communication executed by the second communication units 24 falls within a predetermined range in Step ST31.

When the device 2A determines that the difference in the condition information exceeds the predetermined range (NO in Step ST32), the device 2A skips Step ST33 to proceed to Step ST34. In Step ST34, the device 2A determined whether to operate as the representative device, based on the comparison result in Step ST21 (Step ST34). The determination in Step ST34 in this case is similar to that in Step ST22 (FIG. 4).

When the device 2A determines that the difference in the condition information falls within the predetermined range (YES in Step ST32), the device 2A compares the speed information (Step ST33). In Step ST33, the device 2A calculates a speed of the device 2A, and compares the speed of the device 2A and a speed indicated in the speed information received from the other devices 2. The speed of the device 2A corresponds to an example of a first speed, and the speed indicated in the speed information received by the device 2A from the other devices 2 corresponds to an example of a second speed. The device 2A determines whether the device 2A is to operate as the representative device, based on the speed comparison result (Step ST34). When the device 2 at a higher speed than the device 2A is present, the device 2A determines that the device 2A is not to operate as the representative device (NO in Step ST34). Further, when the speed of the device 2A is higher than the other devices 2, the device 2A determines to operate as the representative device (YES in Step ST34). The processing thereafter is common to that of FIG. 4.

According to the third exemplary embodiment, the device 2 is capable of transmitting the first condition information containing the first speed being the speed of the device 2.

In other words, the device 2 receives, from the other devices 2, the second condition information containing the second speed being the speed of the other devices 2. When a difference between the second condition information received by the first communication unit 23 and the first condition information relating to the device 2 falls within the predetermined range, the device 2 compares the first speed and the second speed. When the first speed is a speed higher than the second speed, the device 2 determines to operate as the representative device.

With this, in the information processing system 100, the device 2 determines whether to operate as the representative device, based on its own first speed and the second speed of the other devices 2. With this, the representative device is selected based on the speed of the device 2. Therefore, a load can be prevented from being imposed on a specific device 2. Moreover, the device 2 moving at a high speed is selected as the representative device, and hence efficiency of the operation of the information processing system 100 can be improved.

A sport event is described above as a usage form of the information processing system 100. For example, it is assumed that each contestant wears the device 2 in a sport event in which a large number of contestants perform time trials regarding a moving time period to a goal, such as a marathon, a triathlon, and a duathlon. In this example, a contestant moving at a high speed is capable of arriving at a goal for a time period shorter than other contestants. Thus, even when an operation time period of the device 2 worn by the contestant is shorter than that of the devices 2 worn by the other contestants, there may not arise a problem. A power consumption amount of the device 2 as described above is increased so as to suppress power consumption of the device 2 of a contestant moving at a lower speed. In this case, in the information processing system 100 as a whole, a larger number of devices 2 can be driven for a long time period. Further, when the difference in the condition information exceeds the predetermined range, the device 2 determines whether to operate as the representative device, based on the condition information. Thus, a load can be prevented from being imposed excessively on a specific device 2.

In this manner, a load can be prevented from being imposed on a specific device 2, and the representative device is selected so that a load of the device 2 moving at a high speed is increased. With this, a large number of devices 2 included in the information processing system 100 can operate for a long time period.

4. Other Exemplary Embodiments

The above-described exemplary embodiments are preferred embodiments of the present disclosure. However, the present disclosure is not limited to thereto, and various modifications may be applied to the exemplary embodiments without departing from the gist of the present disclosure.

For example, in the above-mentioned exemplary embodiments, there is exemplified the configuration in which the device 2 includes the first communication unit 23 that executes near distance communication and the second communication unit 24 that executes LPWA communication or the like in a separate manner. However, those units may be one integrated communication module. In this case, the communication history information 223 may be information indicating the number of times or an executing time period for which the integrated communication module executes LPWA communication.

Each of the functional units of the information processing system 100 illustrated in FIG. 1 represents a functional configuration, and a specific implementation thereof is not particularly limited. Hardware that individually corresponds to each of the illustrated functional units is not required to be implemented, and a configuration is possible as a matter of course in which a single processor executes a program to enable functions of a plurality of functional units. Further, in each of the exemplary embodiments described above, some of the functions realized by software may be realized by hardware, or some of the functions realized by hardware may be realized by software.

Further, a processing unit illustrated in FIG. 3, FIG. 4, FIG. 6, and FIG. 7 is obtained by dividing processing in accordance with a main processing content to facilitate the understanding of the processing of each of the units in the information processing system 100. Thus, the present disclosure is not limited by a method for dividing processing into processing units and a name. The processing may be divided into more processing units in accordance with a processing content, and may be divided such that one processing unit includes more processing.

What is claimed is:

1. An information processing system, comprising:
a server; and
an electronic device configured to:
communicate with another electronic device,
determine whether to operate as a representative device, based on information from the another electronic device, and
when the electronic device determines to operate as the representative device, transmit, to the server, detection information detected by the another electronic device, wherein
when the electronic device determines to operate as the representative device, the electronic device transmits, to the another electronic device, representative device information indicating that the electronic device operates as the representative device, and
when the another electronic device receives the representative device information, the another electronic device determines not to operate as the representative device.

2. The information processing system according to claim 1, wherein
the electronic device compares first condition information and second condition information, and determines whether to operate as the representative device, the first condition information indicating a load condition of the electronic device, and the second condition information indicating a load condition of the another electronic device and being received from the another electronic device.

3. The information processing system according to claim 2, wherein
the first condition information contains a first speed of the electronic device,
the second condition information contains a second speed of the another electronic device, and
when a difference between the first condition information and the second condition information falls within a predetermined range and the first speed is higher than the second speed as a result of comparison between the first speed and the second speed, the electronic device determines to operate as the representative device.

4. The information processing system according to claim 1, wherein
the electronic device receives:
the detection information and
identification information relating to the another electronic device.

5. The information processing system according to claim 4, wherein
the electronic device receives:
position information relating to the another electronic device and
the identification information.

6. The information processing system according to claim 1, wherein
the electronic device periodically determines, with a time interval being a first period, whether to operate as the representative device, and
when the electronic device determines to operate as the representative device, the electronic device periodically executes, with a time interval being a second period, an operation of transmitting the detection information to the server, the second period being shorter than the first period.

7. An electronic device, comprising:
a first communication device configured to communicate with another electronic device;
a second communication device configured to communicate with a server; and
a processor configured to:

determine whether the electronic device is to operate as a representative device, based on information from the another electronic device and when it is determined that the electronic device is to operate as the representative device, transmit, to the server, detection information detected by the another electronic device, wherein when the processor determines the electronic device to operate as the representative device, the processor transmits, to the another electronic device, representative device information indicating that the electronic device operates as the representative device, and when the another electronic device receives the representative device information, the another electronic device determines not to operate as the representative device.

8. The electronic device according to claim 7, wherein the processor compares first condition information and second condition information, and determines whether the electronic device is to operate as the representative device, the first condition information indicating a load condition of the electronic device, and the second condition information indicating a load condition of the another electronic device and being received from the another electronic device.

* * * * *